(12) United States Patent
Hancock et al.

(10) Patent No.: US 6,172,185 B1
(45) Date of Patent: Jan. 9, 2001

(54) ANTIMICROBIAL CATIONIC PEPTIDE DERIVATIVES OF BACTENECIN

(75) Inventors: Robert E. W. Hancock; Manhong Wu, both of Vancouver (CA)

(73) Assignee: University of British Columbia, Vancouver (CA)

( * ) Notice: Under 35 U.S.C. 154(b), the term of this patent shall be extended for 0 days.

(21) Appl. No.: 09/082,420

(22) Filed: May 20, 1998

(51) Int. Cl.[7] ............................. C07K 7/08; A61K 38/10

(52) U.S. Cl. ..................... 530/326; 530/317; 530/327; 514/9; 514/14

(58) Field of Search .................................. 530/326, 327, 530/317; 514/14

(56) References Cited

FOREIGN PATENT DOCUMENTS 0 665 239   8/1995   (EP) .
WO 98 40401   9/1998   (WO) .

OTHER PUBLICATIONS

Storici P. et al., "Purification and structural character of bovine cathelicidins, precursors of antimicrobial peptides", *European Journal of Biochemistry*, vol. 238, No. 3, Jun. 15, 1996, pp. 769–776.

Storici P. et al., "cDNA sequence analysis of an antibiotic dodecapeptide from neutrophils", *FEDS Letters*, vol. 314, No. 2, Dec. 14, 1992, pp. 187–190.

Romeo D. et al., "Structure and bactericidal activity from antibiotic dodecapeptide purified from bovine neutrophils", *Journal of Biological Chemistry*, vol. 263, No. 20, Jul. 15, 1998, pp. 9573–9575.

Gennaro R. et al., "Purification, composition and activity of two bactenecins, antibacterial peptides of bovine neutrophils", *Infection and Immunity, US, American Society for Microbiology, Washington*, vol. 57, No. 10, Oct. 1989, pp. 0019–9567.

*Primary Examiner*—Michael Borin
(74) *Attorney, Agent, or Firm*—Gray Cary Ware & Freidenrich LLP; Lisa A. Haile

(57) ABSTRACT

A novel class of cationic peptides having antimicrobial activity is provided. Exemplary peptides of the invention include RLARIVVIRVAR (SEQ ID NO:2) and RLSRIVVIRVCR (SEQ ID NO:3). Also provided are methods for inhibiting the growth of bacteria utilizing the peptides of the invention.

2 Claims, 6 Drawing Sheets

```
                           SEQUENCE LISTING

<160> NUMBER OF SEQ ID NOS: 20

<210> SEQ ID NO 1
<211> LENGTH: 12
<212> TYPE: PRT
<213> ORGANISM: Artificial Sequence
<220> FEATURE:
<223> OTHER INFORMATION: cationic antimicrobial peptide

<400> SEQUENCE: 1

Arg Leu Cys Arg Ile Val Val Ile Arg Val Cys Arg
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 2

Arg Leu Ala Arg Ile Val Val Ile Arg Val Ala Arg
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 3

Arg Leu Ser Arg Ile Val Val Ile Arg Val Cys Arg
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 4

Arg Leu Ser Arg Ile Val Val Ile Arg Val Ser Arg
 1               5                  10

<210> SEQ ID NO 5
<211> LENGTH: 12
```

-continued

```
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 5

Arg Arg Cys Pro Ile Val Val Ile Arg Val Cys Arg
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 6

Arg Ile Cys Arg Ile Val Val Ile Arg Cys Ile Arg
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 7

Arg Leu Cys Pro Arg Val Arg Ile Arg Val Cys Arg
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: cationic antimicrobial peptide

<400> SEQUENCE: 8

Lys Lys Cys Pro Ile Val Val Ile Arg Val Cys Lys
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: cationic antimicrobial peptide

<400> SEQUENCE: 9

Arg Arg Arg Cys Pro Ile Val Val Ile Arg Val Cys Arg Arg
 1               5                  10

<210> SEQ ID NO 10
<211> LENGTH: 14
<212> TYPE: PRT
<213> ORGANISM: Artificial Sequence
```

```
<220> FEATURE:
<223> OTHER INFORMATION: cationic antimicrobial peptide

<400> SEQUENCE: 10

Arg Arg Arg Leu Cys Pro Ile Val Ile Arg Val Cys Arg Arg
 1               5                  10

<210> SEQ ID NO 11
<211> LENGTH: 14
<212> TYPE: PRT
<213> ORGANISM: Artificial Sequence
<220> FEATURE:
<223> OTHER INFORMATION: cationic antimicrobial peptide

<400> SEQUENCE: 11

Arg Arg Leu Cys Arg Ile Val Val Ile Arg Val Cys Arg Arg
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: cationic antimicrobial peptide

<400> SEQUENCE: 12

Arg Leu Cys Arg Ile Val Pro Val Ile Arg Val Cys Arg
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: cationic antimicrobial peptide

<400> SEQUENCE: 13

Arg Leu Cys Arg Ile Val Trp Val Ile Arg Val Cys Arg
 1               5                  10

<210> SEQ ID NO 14
<211> LENGTH: 15
<212> TYPE: PRT
<213> ORGANISM: Artificial Sequence
<220> FEATURE:
<223> OTHER INFORMATION: cationic antimicrobial peptide

<400> SEQUENCE: 14

Arg Arg Leu Cys Arg Ile Val Trp Val Ile Arg Val Cys Arg Arg
 1               5                  10                  15

<210> SEQ ID NO 15
<211> LENGTH: 13
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 15

Arg Arg Cys Pro Ile Val Trp Val Ile Arg Val Cys Arg
 1               5                  10

<210> SEQ ID NO 16
```

```
<211> LENGTH: 14
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 16

Arg Arg Cys Pro Ile Val Trp Val Ile Pro Val Cys Arg Arg
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: cationic antimicrobial peptide
<220> FEATURE:
<221> NAME/KEY: AMIDATION
<222> LOCATION: (0)...(0)
<223> OTHER INFORMATION: amidated Arg at C-terminus

<400> SEQUENCE: 17

Arg Leu Cys Arg Ile Val Val Ile Arg Val Cys Arg
 1               5                  10

<210> SEQ ID NO 18
<211> LENGTH: 18
<212> TYPE: PRT
<213> ORGANISM: Artificial Sequence
<220> FEATURE:
<223> OTHER INFORMATION: cationic antimicrobial peptide

<400> SEQUENCE: 18

Arg Leu Cys Arg Ile Val Val Ile Arg Val Cys Arg Ile Val Ile Val
 1               5                  10                  15

Ile Val

<210> SEQ ID NO 19
<211> LENGTH: 12
<212> TYPE: PRT
<213> ORGANISM: Artificial Sequence
<220> FEATURE:
<223> OTHER INFORMATION: cationic antimicrobial peptide

<400> SEQUENCE: 19

Arg Leu Ser Arg Ile Val Val Ile Arg Val Ser Arg
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: cationic antimicrobial peptide

<400> SEQUENCE: 20

Arg Arg Cys Pro Ile Val Val Ile Arg Val Cys Arg
 1               5                  10
```

ANTIMICROBIAL CATIONIC PEPTIDE DERIVATIVES OF BACTENECIN

BACKGROUND OF THE INVENTION

1. Field of the Invention

This invention relates generally to antimicrobial peptides and specifically to derivatives of the antimicrobial cationic peptide, bactenecin.

2. Description of Related Art

In 1981, the self-promoted uptake hypothesis was first proposed to explain the mechanism of action of polycationic antibiotics in *Pseudomonas aeruginosa*. According to this hypothesis, polycations interact with sites on the outer membranes of Gram-negative bacteria at which divalent cations cross-bridge adjacent lipopolysaccharide molecules. Due to their higher affinity for these sites, polycations displace the divalent cations and, since the polycations are bulkier than the divalent cations, cause structural perturbations in the outer membrane. These perturbations result in increased outer membrane permeability to compounds such as the β-lactam antibiotic nitrocefin, the eukaryotic non-specific defense protein lysozyme and to hydrophobic substances. By analogy, molecules accessing this pathway are proposed to promote their own uptake.

It has been clearly demonstrated that the outer membranes of Gram-negative bacteria are semipermeable molecular "sieves" which restrict access of antibiotics and host defense molecules to their targets within the bacterial cell. Thus, cations and polycations which access the self-promoted uptake system are, by virtue of their ability to interact with and break down the outer membrane permeability barrier, capable of increasing the susceptibility of Gram-negative pathogenic bacteria to antibiotics and host defense molecules. Hancock and Wong demonstrated that a broad range of such compounds could overcome the permeability barrier and coined the name "permeabilizers" to describe them (Hancock and Wong, *Antimicrob. Agents Chemother.*, 26:48, 1984). While self-promoted uptake and permeabilizers were first described for *P. aeruginosa*, they have now been described for a variety of Gram-negative bacteria.

Over the past decade, non-specific defense molecules have been described in many animals, including insects and humans. One subset of these molecules have in common the following features: (a) they are small peptides, usually 15–35 amino acids in length, (b) they contain 4 or more positively charged amino acid residues, either lysines or arginines, and (c) they are found in high abundance in the organisms from which they derive. Several of these molecules have been isolated, amino acid sequenced and described in the patent literature (e.g., cecropins: WO 8900199, WO 8805826, WO 8604356, WO 8805826; defensins: EP 193351, EP 85250, EP 162161, U.S. Pat. No. 4,659,692, WO 8911291). However, only limited amounts of these peptides can be isolated from the host species. For example, Sawyer, et al., (*Infect. Immun.* 56:693, 1988) isolated 100–200 mg of rabbit neutrophil defensins 1 and 2 from $10^9$ primed peritoneal neutrophils or lipopolysaccharide-elicited alveolar macrophages (i.e., the numbers present in a whole animal).

The gene for human defensin has been cloned and sequenced, but no successful expression has been demonstrated, as yet. Furthermore, production of these peptides using peptide synthesis technology produces peptides in limited amounts and is expensive when scaled up or when many variant peptides must be produced. Also, structural analysis is difficult without specific incorporation of $^{15}N$ and $^{13}C$ tagged amino acids which is prohibitively expensive using amino acid synthesis technology.

Recently, cationic peptides containing a disulphide bond forming a looped structure were identified (Morikawa et al., *Biochim. Biophys. Res. Commun.* 189:184, 1992; Simmaco et al., *FEBS* 324:159, 1993; Clark et al., *J. Biol. Chem.* 269:10849, 1994). One member of this group, bactenecin (i.e., dodecapeptide), is a twelve amino acid peptide isolated from bovine neutrophils (Romeo et al., *J Biol. Chem.* 263:9573, 1988). Bactenecin is the smallest known cationic antimicrobial peptide. Two cysteine residues form a disulphide bond to make bactenecin a loop molecule. Bactenecin was previously found to be active against *Escherischia coli* and *Staphylococcus aureus*, and strongly cytotoxic for rat embryonic neurons, fetal rat astrocytes and human glioblastoma cells (Radermacher et al., *J. Neuroscience Res.* 36:657, 1993).

There is a need to develop peptides having a broad range of potent antimicrobial activity against a plurality of microorganisms, including gram negative bacteria, gram positive bacteria, fungi, protozoa, viruses and the like. To that end, the small size and structure of bactenecin present an opportunity to identify derivatives of the polypeptide which are effective as therapeutics for microbial pathogens.

SUMMARY OF THE INVENTION

The present invention provides derivatives of the antimicrobial cationic peptide bactenecin, that have antimicrobial activity. In a first embodiment, the invention provides antimicrobial peptides derived from bactenecin. Exemplary peptides include: RLCRIVVIRVCR (SEQ ID NO:1); RLARIVVIRVAR NH₂ (SEQ ID NO:2); RLSRIVVIRVCR NH₂ (SEQ ID NO:3); RLSRIVVRVSR NH₂ (SEQ ID NO:4); RRCPIVVIRVCR NH₂ (SEQ ID NO:5); RICRIVVIRCIR (SEQ ID NO:6); RLCPRVRIRVCR NH₂ (SEQ ID NO:7); KKCPIVVIRVCK (SEQ ID NO:8); RRRCPIVVIRVCRR (SEQ ID NO:9); RRRLCPIVIRVCRR (SEQ ID NO:10); RRLCRIVVIRVCRR (SEQ ID NO:11); RLCRIVPVIRVCR (SEQ ID NO:12); RLCRIVWVIRVCR (SEQ ID NO:13); RRLCRIVWVIRVCRR (SEQ ID NO:14); RRCPIVWVIRVCR NH₂ (SEQ ID NO:15); RRCPIVWVIPVCRR NH₂ (SEQ ID NO:16); RLCRIVVIRVCR NH₂ (SEQ ID NO:17); RLCRIVVIRVCRIVIVIV (SEQ ID NO:18); RLSRIVVIRVSR (SEQ ID NO:19); and RRCPIVVIRVCR (SEQ ID NO: 20), and analogs, derivatives, amidated variations and conservative variations thereof.

The invention also provides a method of inhibiting the growth of bacteria including contacting the bacteria with an inhibiting effective amount of at least one peptide of the invention alone, or in combination with at least antibiotic. Classes of antibiotics that can be used in synergistic therapy with the peptides of the invention include aminoglycoside, penicillin, cephalosporine, fluoroquinolone, carbepenem, tetracycline and macrolide.

The invention further provides polynucleotides that encode the peptides of the invention. Exemplary polynucleotides encode peptides including: RLCRIVVIRVCR (SEQ ID NO:1); RLARIVVIRVAR NH₂ (SEQ ID NO:2); RLSRIVVIRVCR NH₂ (SEQ ID NO:3); RLSRIVVIRVSR NH₂ (SEQ ID NO:4); RRCPIVVIRVCR NH₂ (SEQ ID NO:5); RICRIVVIRCIR NH2 (SEQ ID NO:6); RLCPRVRIRVCR NH₂ (SEQ ID NO:7); KKCPIVVIRVCK (SEQ ID NO:8); RRRCPIVVIRVCRR (SEQ ID NO:9); RRRLCPIVIRVCRR (SEQ ID NO:10); RRLCRIVVIRVCRR (SEQ ID NO:11); RLCRIVPVIRVCR (SEQ ID NO:12); RLCRIVWVIRVCR (SEQ ID NO:13); RRLCRIVWVIRVCRR (SEQ ID NO:14); RRCPIVWVIRVCR NH$_2$ (SEQ ID NO:15); RRCPIVWVIPVCRR NH$_2$ (SEQ ID NO:16); RLCRIVVIRVCR NH$_2$ (SEQ ID NO:17); RLCRIV-VIRVCRIVIVIV (SEQ ID NO:18); RLSRIVVIRVSR (SEQ ID NO:19); and RRCPIVVIRVCR (SEQ ID NO: 20), and analogs, derivatives and conservative variations thereof.

In another embodiment, the invention provides a method of inhibiting an endotoxemia or sepsis associated disorder in a subject having or at risk of having such a disorder, by administering to the subject a therapeutically effective amount of at least one peptide of the invention.

The invention also provides a method of inhibiting the growth of a eukaryotic cell. The method includes contacting the cell with an inhibiting effective amount of a peptide or combination thereof of the invention, alone, or in combination with an agent effective for inhibiting eukaryotic cell growth. Classes of such agents which can be used for synergistic therapy with the peptides of the invention include bleomycin, neocarcinostatin, suramin, doxorubicin, taxol, mitomycin C and cisplatin.

The invention further provides a method of inhibiting a cell proliferation-associated disorder in a subject having or at risk of having such a disorder. The method includes administering to the subject a therapeutically effective amount of at least one peptide of the invention, alone, or in combination with an agent effective for inhibiting eukaryotic cell growth. Classes of such agents which can be used for synergistic therapy with the peptides of the invention include bleomycin, neocarcinostatin, suramin, doxorubicin, taxol, mitomycin C and cisplatin.

BRIEF DESCRIPTION OF THE DRAWINGS

FIG. 1 shows the CD spectra of bactenecin in its reduced form and bac2S in phosphate buffer, in the presence POPC/POPG liposomes, in 60% TFE and in 10 mM SDS. The concentrations of peptides and liposomes were 50 μM and 100 μM, respectively. CD measurements were taken in 10 mM sodium phosphate buffer (pH 7.0) in the absence (panel A) and the presence (panel B) of POPC/POPG. Panel C shows the spectra in the presence of 60% (v/v) TFE. Bactenecin: . . . ; Reduced bactenecin: ____; Bac2S: - - - .

DETAILED DESCRIPTION OF THE INVENTION

Figure 1A:
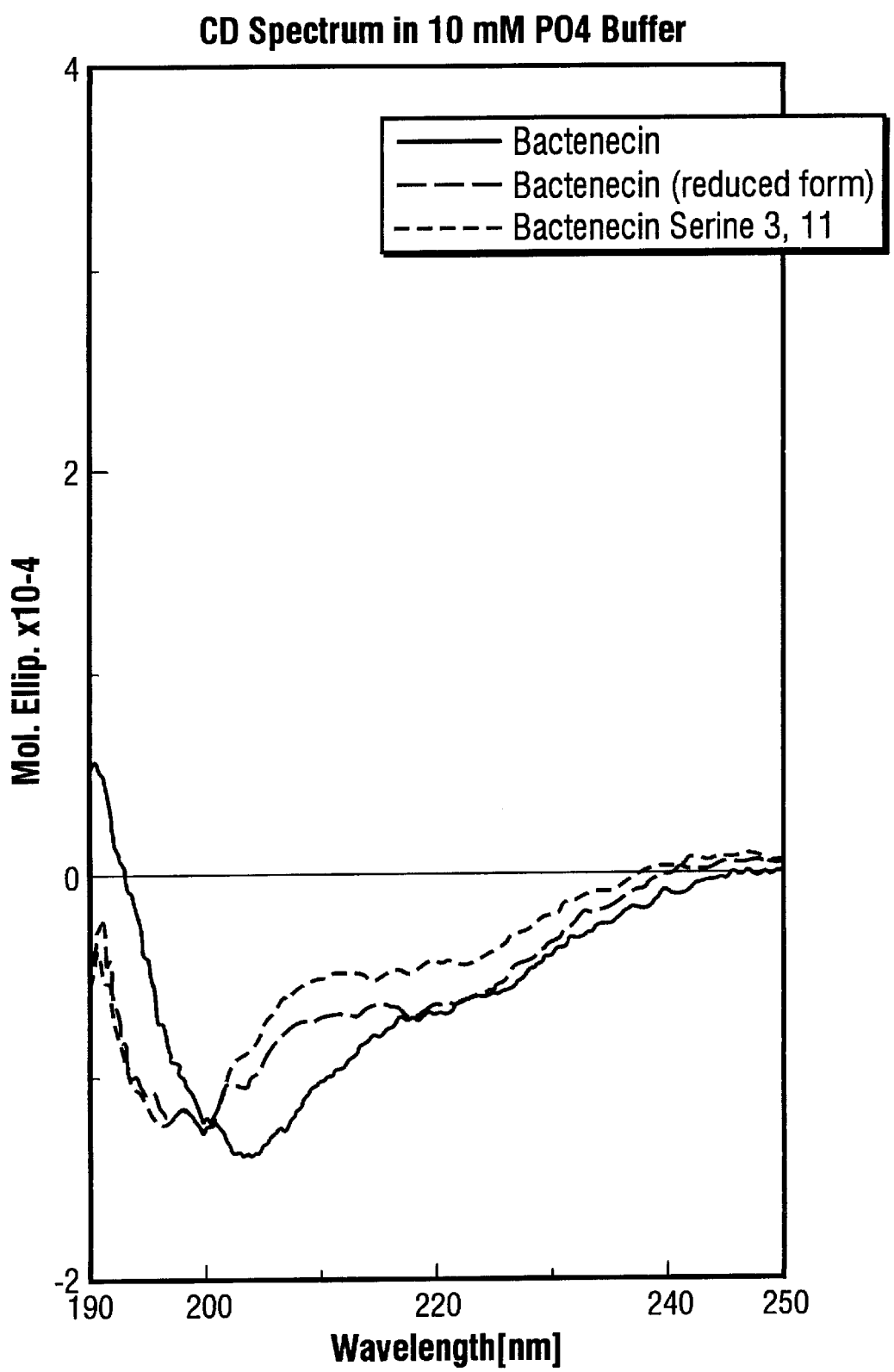
FIG. 1A shows the CD spectra of bactenecin in 10 mM sodium phosphate buffer (pH 7.0) in the absence of POPC/POPG.

The present invention provides derivatives of bactenecin, an antimicrobial cationic peptide, which have antimicrobial activity. These peptides are useful for inhibiting microbial infection or growth, as well reducing the effects of endotoxemia, and are often synergistic with conventional antibiotics and/or lysozyme. In addition, such peptides are useful as antifungal agents, antitumor agents, or antiviral agents.

The term "antimicrobial" as used herein means that the peptides of the present invention inhibit, prevent, or destroy the growth or proliferation of microbes such as bacteria, fungi, viruses, parasites or the like. The term "antiviral" as used herein means that the peptides of the present invention inhibit, prevent or destroy the growth or proliferation of viruses or of virally-infected cells. The term "anti-tumor" as used herein means that the peptides of the present invention may be used to inhibit the growth of or destroy tumors. The term "antifungal" as used herein means that the peptides of the present invention may be used to inhibit the growth of or destroy fungi. The term "antiparasite", as used herein, means that the peptides of the present invention inhibit, prevent, or destroy the growth or proliferation of any organism that lives at the expense of a host organism.

In a first embodiment, the invention provides an isolated antimicrobial peptide derived from bactanecin. Exemplary peptides of the invention have an amino acid sequence including: RLCRIVVIRVCR (SEQ ID NO:1); RLARIV-VIRVAR NH$_2$ (SEQ ID NO:2); RLSRIVVIRVCR NH$_2$ (SEQ ID NO:3); RLSRIVVIRVSR NH$_2$ (SEQ ID NO:4); RRCPIVVIRVCR NH$_2$ (SEQ ID NO:5); RICRIVVIRCIR NH$_2$ (SEQ ID NO:6); RLCPRVRIRVCR NH$_2$ (SEQ ID NO:7); KKCPIVVIRVCK (SEQ ID NO:8); RRRCPIV-VIRVCRR (SEQ ID NO:9); RRRLCPIVIRVCRR (SEQ ID NO:10); RRLCRIVVIRVCRR (SEQ ID NO:11); RLCRIV-PVIRVCR (SEQ ID NO:12); RLCRIVWVIRVCR (SEQ ID NO:13); RRLCRIVWVIRVCRR (SEQ ID NO:14); RRCPIVWVIRVCR NH$_2$ (SEQ ID NO:15); RRCPIV-WVIPVCRR NH$_2$ (SEQ ID NO:16); RLCRIVVIRVCR NH$_2$ (SEQ ID NO:17); RRCPIVWVIPVCRR NH$_2$ (SEQ ID NO:16); RLCRIVVIRVCR NH$_2$ (SEQ ID NO:17); RLCRIVVIRVCRIVIVIV (SEQ ID NO:18); RLSRIV-VIRVSR (SEQ ID NO:19); and RRCPIVVIRVCR (SEQ ID NO: 20), and analogs, derivatives, amidated variations and conservative variations thereof, wherein the peptides have antimicrobial activity. The peptides of the invention include SEQ ID NOS:1–18, as well as the broader groups of peptides having hydrophilic and hydrophobic substitutions, and conservative variations thereof.

The term "isolated" as used herein refers to a peptide substantially free of proteins, lipids, nucleic acids, for example, with which it is naturally associated. Those of skill in the art can make similar substitutions to achieve peptides with greater antimicrobial activity and a broader host range. For example, the invention includes the bactenecin derivative peptides depicted in SEQ ID NO:1–18, as well as analogues or derivatives thereof, as long as the bioactivity (e.g., antimicrobial) of the peptide remains. Minor modifications of the primary amino acid sequence of the peptides of the invention may result in peptides which have substantially equivalent activity as compared to the specific peptides described herein. Such modifications may be deliberate, as by site-directed mutagenesis, or may be spontaneous. All of the peptides produced by these modifications are included herein as long as the biological activity of the original peptide still exists.

Further, deletion of one or more amino acids can also result in a modification of the structure of the resultant molecule without significantly altering its biological activity. This can led to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, so long as the bioactivity as described herein is remains. All peptides were synthesized using L amino acids, however, all D forms of the peptides (e.g., see Table 1) can be synthetically produced. In addition, C-terminal derivatives can be produced, such as C-terminal methyl esters and C-terminal amidates (e.g., see table I), in order to increase the antimicrobial activity of a peptide of the invention. "Peptide" of the invention includes peptides which are conservative variations of those peptides specifically exemplified herein. The term "conservative variation" as used herein denotes the replacement of an amino acid residue by another, biologically similar residue. Examples of conservative variations include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. The term "conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention.

The biological activity of the peptides can be determined by standard methods known to those of skill in the art, such as "minimal inhibitory concentration (MIC)" assay described in the present examples, whereby the lowest concentration at which no change in OD is observed for a given period of time is recorded as MIC. Alternatively, "fractional inhibitory concentration (FIC)" is also useful for determination of synergy between the peptides of the invention, or the peptides in combination with known antibiotics. FICs are performed by checkerboard titrations of peptides in one dimension of a microtiter plate, and of antibiotics in the other dimension, for example. The FIC is calculated by looking at the impact of one antibiotic on the MIC of the other and vice versa. An FIC of one indicates that the influence of the compounds is additive and an FIC of less than one indicates synergy. Preferably, an FIC of less than 0.5 is obtained for synergism. As used herein, FIC can be determined as follows:

$$FIC = \frac{MIC(\text{peptide in combination})}{MIC(\text{peptide alone})} + \frac{MIC(\text{antibiotic in combination})}{MIC(\text{antibiotic alone})}$$

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention includes polynucleotides encoding peptides of the invention. Exemplary polynucleotides encode peptides including: RLCRIVVIRVCR (SEQ ID NO:1); RLARIVVIRVAR $NH_2$ (SEQ ID NO:2); RLSRIVVIRVCR $NH_2$ (SEQ ID NO:3); RLSRIVVIRVSR $NH_2$ (SEQ ID NO:4); RRCPIVVIRVCR $NH_2$ (SEQ ID NO:5); RICRIVVIRCIR $NH_2$ (SEQ ID NO:6); RLCPRVRIRVCR $NH_2$ (SEQ ID NO:7); KKCPIVVIRVCK (SEQ ID NO:8); RRRCPIVVIRVCRR (SEQ ID NO:9); RRRLCPIVIRVCRR (SEQ ID NO:10); RRLCRIVVIRVCRR (SEQ ID NO:11); RLCRIVPVIRVCR (SEQ ID NO:12); RLCRIVWVIRVCR (SEQ ID NO:13); RRLCRIVWVIRVCRR (SEQ ID NO:14); RRCPIVWVIRVCR $NH_2$ (SEQ ID NO:15); RRCPIVWVIPVCRR $NH_2$ (SEQ ID NO:16); RLCRIVVIRVCR $NH_2$ (SEQ ID NO:17); RLCRIVVIRVCRIVIVIV (SEQ ID NO:18); RLSRIVVIRVSR (SEQ ID NO:19); and RRCPIVVIRVCR (SEQ ID NO: 20), and analogs, derivatives, amidated variations and conservative variations thereof, wherein the peptides have antimicrobial activity. The peptides of the invention include SEQ ID NOS:1–18, as well as the broader groups of peptides having hydrophilic and hydrophobic substitutions, and conservative variations thereof.

The term "isolated" as used herein refers to a polynucleotide substantially free of proteins, lipids, nucleic acids, for example, with which it is naturally associated. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code. Such polynucleotides are useful for the recombinant production of large quantities of a peptide of interest, such as the peptide of SEQ ID NO:1–18.

In the present invention, the polynucleotides encoding the cationic peptides of the invention may be inserted into a recombinant "expression vector". The term "expression vector" refers to a plasmid, virus or other vehicle known in the art that has been manipulated by insertion or incorporation of cationic genetic sequences. Such expression vectors of the invention are preferably plasmids which contain a promoter sequence which facilitates the efficient transcription of the inserted genetic sequence in the host. The expression vector typically contains an origin of replication, a promoter, as well as specific genes which allow phenotypic selection of the transformed cells. For example, the expression of the peptides of the invention can be placed under control of $E.$ $coli$ chromosomal DNA comprising a lactose or lac operon which mediates lactose utilization by elaborating the enzyme beta-galactosidase. The lac control system can be induced by IPTG. A plasmid can be constructed to contain the lac Iq repressor gene, permitting repression of the lac promoter until IPTG is added. Other promoter systems known in the art include beta lactamase, lambda promoters, the protein A promoter, and the tryptophan promoter systems. While these are the most commonly used, other microbial promoters, both inducible and constitutive, can be utilized as well. The vector contains a replicon site and control sequences which are derived from species compatible with the host cell. In addition, the vector may carry specific gene(s) which are capable of providing phenotypic selection in transformed cells. For example, the beta-lactamase gene confers ampicillin resistance to those transformed cells containing the vector with the beta-lactamase gene. An exemplary expression system for production of the peptides of the invention is described in U.S. Pat. No. 5,707,855.

Transformation of a host cell with the polynucleotide may be carried out by conventional techniques well known to those skilled in the art. For example, where the host is prokaryotic, such as $E.$ $coli$, competent cells which are capable of DNA uptake can be prepared from cells harvested after exponential growth and subsequently treated by the $CaCl_2$ method using procedures well known in the art. Alternatively, $MgCl_2$ or RbCl could be used.

In addition to conventional chemical methods of transformation, the plasmid vectors of the invention may be introduced into a host cell by physical means, such as by electroporation or microinjection. Electroporation allows transfer of the vector by high voltage electric impulse, which creates pores in the plasma membrane of the host and is performed according to methods well known in the art. Additionally, cloned DNA can be introduced into host cells by protoplast fusion, using methods well known in the art.

DNA sequences encoding the cationic peptides can be expressed in vivo by DNA transfer into a suitable host cell.

"Host cells" of the invention are those in which a vector can be propagated and its DNA expressed. The term also includes any progeny of the subject host cell. It is understood that not all progeny are identical to the parental cell, since there may be mutations that occur during replication. However, such progeny are included when the terms above are used. Preferred host cells of the invention include $E.$ $coli,$ $S.$ $aureus$ and $P.$ $aeruginosa$, although other Gram-negative and Gram-positive organisms known in the art can be utilized as long as the expression vectors contain an origin of replication to permit expression in the host.

The cationic peptide polynucleotide sequence used according to the method of the invention can be isolated from an organism or synthesized in the laboratory. Specific DNA sequences encoding the cationic peptide of interest can be obtained by: 1) isolation of a double-stranded DNA sequence from the genomic DNA; 2) chemical manufacture of a DNA sequence to provide the necessary codons for the cationic peptide of interest; and 3) in vitro synthesis of a double-stranded DNA sequence by reverse transcription of mRNA isolated from a donor cell. In the latter case, a double-stranded DNA complement of mRNA is eventually formed which is generally referred to as cDNA.

The synthesis of DNA sequences is frequently the method of choice when the entire sequence of amino acid residues of the desired peptide product is known. In the present invention, the synthesis of a DNA sequence has the advantage of allowing the incorporation of codons which are more likely to be recognized by a bacterial host, thereby permitting high level expression without difficulties in translation. In addition, virtually any peptide can be synthesized, including those encoding natural cationic peptides, variants of the same, or synthetic peptides.

When the entire sequence of the desired peptide is not known, the direct synthesis of DNA sequences is not possible and the method of choice is the formation of cDNA sequences. Among the standard procedures for isolating cDNA sequences of interest is the formation of plasmid or phage containing cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the cationic peptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., $Nuc.$ $Acid$ $Res.$, 11:2325, 1983).

The invention also provides a method of inhibiting the growth of bacteria including contacting the bacteria with an inhibiting effective amount of a peptide of the invention, including:RLCRIVVIRVCR (SEQ ID NO:1); RLARIVVIRVAR $NH_2$ (SEQ ID NO:2); RLSRIVVIRVCR $NH_2$ (SEQ ID NO:3); RLSRIVVIRVSR $NH_2$ (SEQ ID NO:4); RRCPIVVIRVCR $NH_2$ (SEQ ID NO:5); RICRIVVIRCIR $NH_2$ (SEQ ID NO:6); RLCPRVRIRVCR $NH_2$ (SEQ ID NO:7); KKCPIVVIRVCK (SEQ ID NO:8); RRRCPIVVIRVCRR (SEQ ID NO:9); RRRLCPIVIRVCRR (SEQ ID NO:10); RRLCRIVVIRVCRR (SEQ ID NO:11); RLCRIVPVIRVCR (SEQ ID NO:12); RLCRIVWVIRVCR (SEQ ID NO:13); RRLCRIVWVIRVCRR (SEQ ID NO:14); RRCPIVWVIRVCR $NH_2$ (SEQ ID NO:15); RRCPIVWVIPVCRR $NH_2$ (SEQ ID NO:16); RLCRIVVIRVCR $NH_2$ (SEQ ID NO:17); RLCRIVVIRVCRIVIVIV (SEQ ID NO:18); RLSRIVVIRVSR (SEQ ID NO:19); and RRCPIV-VIRVCR (SEQ ID NO: 20), and analogs, derivatives, amidated variations and conservative variations thereof, wherein the peptides have antimicrobial activity.

The term "contacting" refers to exposing the bacteria to the peptide so that the peptide can effectively inhibit, kill, or lyse bacteria, bind endotoxin (LPS), or permeabilize gram-negative bacterial outer membranes. Contacting may be in vitro, for example by adding the peptide to a bacterial culture to test for susceptibility of the bacteria to the peptide. Contacting may be in vivo, for example administering the peptide to a subject with a bacterial disorder, such as septic shock. "Inhibiting" or "inhibiting effective amount" refers to the amount of peptide which is required to cause a bacteriostatic or bactericidal effect. Examples of bacteria which may be inhibited include *Escherichia coli, Pseudomonas aeruginosa, Enterobacter cloacae, Staphylococcus typhimurium, Staphylococcus aureus, Enterobacter facaelis, Listeria monocytogenes, Corynebacterium xerosis, Streptococcus pyogenes, Streptococcus pneumoniae, Streptococcus mitis* and *Staphylococcuus epidermidis.*

The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art. Examples of particular classes of antibiotics useful for synergistic therapy with the peptides of the invention include aminoglycosides (e.g., tobramycin), penicillins (e.g., piperacillin), cephalosporins (e.g., ceftazidime), fluoroquinolones (e.g., ciprofloxacin), carbapenems (e.g., imipenem), tetracyclines and macrolides (e.g., erythromycin and clarithromycin). The method of inhibiting the growth of bacteria may further include the addition of antibiotics for combination or synergistic therapy. The appropriate antibiotic administered will typically depend on the susceptibility of the bacteria such as whether the bacteria is gram negative or gram positive, and will be easily discernable by one of skill in the art. Further to the antibiotics listed above, typical antibiotics include aminoglycosides (amikacin, gentamicin, kanamycin, netilmicin, t-obramycin, streptomycin, azithromycin, clarithromycin, erythromycin, erythromycin e-stolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin.

The peptides and/or analogues or derivatives thereof may be administered to any host, including a human or non-human animal, in an amount effective to inhibit not only growth of a bacterium, but also a virus, parasite or fungus. These peptides are useful as antimicrobial agents, antiviral agents, and antifungal agents. The peptides and/or analogues or derivatives thereof may be administered to any host, including a human or non-human animal, in an amount effective to inhibit not only growth of a bacterium, but also a virus or fungus. These peptides are useful as antimicrobial agents, antiviral agents, and antifungal agents.

In addition to being active against a broad range of pathogens, bactenecin has been shown to be cytotoxic to rat embryonic neurons, fetal rat astrocytes and human glioblastoma cells (Radermacher et al., *J. Neuro. Res.* 36:657, 1993). Thus, it is envisioned that the bactenecin derivative peptides of the present invention can be used to inhibit the growth of a eukaryotic cell by contacting the eukaryotic cell with an inhibiting effective amount of a peptide of the invention. Such a method would be useful, for example, for inhibiting a cell proliferation-associated disorder in a subject having or at risk of having such a disorder. The method can involve, for example, administering to the subject a therapeutically effective amount of a peptide of the present invention to inhibit the over-growth of cells in a subject in need of such treatment. Such disorders would include, for example, neurological related disorders.

In a further embodiment, the peptides of the invention can be administered in combination with at least one chemotherapeutic agent useful for treating a cell proliferation-associated disorder, such as a neoplastic disorder. Examples of such chemotherapeutic agents include, but are not limited to, bleomycin, neocarcinostatin, suramin, doxorubicin, taxol, mitomycin C and cisplatin. Such neoplastic disorders would include, for example, neuroblastomas, glioblastomas and astrocytomas.

The peptide of the invention can be administered parenterally by injection or by gradual infusion over time. The peptide can be administered intravenously, intraperitoneally, intramuscularly, subcutaneously, intracavity, or transdermally. Further methods for delivery of the peptide include orally, by encapsulation in microspheres or proteinoids, by aerosol delivery to the lungs, or transdermally by iontophoresis or transdermal electroporation. The method of the invention also includes delivery systems such as microencapsulation of peptides into liposomes. Microencapsulation also allows co-entrapment of antimicrobial molecules along with the antigens, so that these molecules, such as antibiotics, may be delivered to a site in need of such treatment in conjunction with the peptides of the invention. Liposomes in the blood stream are generally taken up by the liver and spleen. Thus, the method of the invention is particularly useful for delivering antimicrobial peptides to such organs. Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention provides a method of treating or ameliorating an endotoxemia or septic shock (sepsis) associated disorder, or one or more of the symptoms of sepsis comprising administering to a subject displaying symptoms of sepsis or at risk for developing sepsis, a therapeutically effective amount of a cationic peptide of the invention, for example, SEQ ID NOS:1–18, or analogs, derivatives, amidated variations or conservative variations thereof. The term "ameliorate" refers to a decrease or lessening of the symptoms of the disorder being treated. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *Escherichia coli, Haemophilus influenza B, Neisseria meningitides*, staphylococci, or pneumococci. Patients at risk for sepsis include those suffering from gunshot wounds, renal or hepatic failure, trauma, burns, immunocompromised (HIV), hematopoietic neoplasias, multiple myeloma, Castleman's disease or cardiac myxoma.

The term "therapeutically effective amount" as used herein for treatment of endotoxemia refers to the amount of cationic peptide used is of sufficient quantity to decrease the subject's response to LPS and decrease the symptoms of sepsis. The term "therapeutically effective" therefore includes that the amount of cationic peptide sufficient to prevent, and preferably reduce by at least 50%, and more preferably sufficient to reduce by 90%, a clinically significant increase in the plasma level of TNF. The dosage ranges for the administration of cationic peptide are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of cationic peptide, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature*, 330:662, 1987).

A patient who exhibits the symptoms of sepsis may be treated with an antibiotic in addition to the treatment with cationic peptide. Typical antibiotics include an aminoglycoside, such as gentamicin or a beta-lactam such as penicillin, or cephalosporin or any of the antibiotics as previously listed above. Therefore, a preferred therapeutic method of the invention includes administering a therapeutically effective amount of cationic peptide substantially simultaneously with administration of a bactericidal amount of an antibiotic. Preferably, administration of cationic peptide occurs within about 48 hours and preferably within about 2–8 hours, and most preferably, substantially concurrently with administration of the antibiotic.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

Because of the antibiotic, antimicrobial, and antiviral properties of the peptides, they may also be used as preservatives or sterillants of materials susceptible to microbial or viral contamination. The peptides of the invention can be utilized as broad spectrum antimicrobial agents directed toward various specific applications. Such applications include use of the peptides as preservatives in processed foods (organisms including Salmonella, Yersinia, Shigella), either alone or in combination with antibacterial food additives such as lysozymes; as a topical agent (Pseudomonas, Streptococcus) and to kill odor producing microbes (Micrococci). The relative effectiveness of the cationic peptides of the invention for the applications described can be readily determined by one of skill in the art by determining the sensitivity of any organism to one of the peptides.

The following examples are intended to illustrate but not limit the invention. While they are typical of those that might be used, other procedures known to those skilled in the art may alternatively be used.

EXAMPLE 1

BACTENECIN DERIVATIVES

Bactenecin was isolated from bovine neutrophils. It has an amino acid sequence of RLCRIVVIRVCR (SEQ ID NO:1), with two cysteine residues forming one disulphide (termed native bactenecin or oxidized bactenecin below), and its C-terminus is unamidated according to the publications presented to date. Moderate activity against three gram-negative bacteria, *Escherichia coli, Pseudomonas aeruginosa* and *Salmonella typhimurium* was observed. A series of derivatives were made (Table I). The bactenecin derivatives were divided into three groups, linear, positive-charge and hydrophobicity.

TABLE I

Amino Acid Sequences of Bactenecin and its Derivatives

| Peptide Classification | Name | Amino Acid Sequence | SEQ ID NO: |
|---|---|---|---|
| Native | Bactenecin | RLCRIVVIRVCR | 1 |
| Linear | Bac 2A-NH2 | RLARIVVIRVAR-NH2 | 2 |
| | Bac 1S-NH2 | RLSRIVVIRVCR-NH2 | 3 |
| | Bac 2S-NH2 | RLSRIVVIRVSR-NH2 | 4 |
| | Bac 2S | RLSRIVVIRVSR | 19 |
| | Bac (Reduced) | RLCRIVVIRVCR | 1 |
| Positive Charge | Bac R, P-NH2 | RRCPIVVIRVCR-NH2 | 5 |
| | Bac R,P | RRCPIVVIRVCR | 20 |
| | Bac 2I-NH2 | RICRIVVIRCIR-NH2 | 6 |
| | Bac P, 2R-NH2 | RLCPRVRIRVCR-NH2 | 7 |
| | Bac 3K, P | KKCPIVVIRVCK | 8 |
| | Bac 3R, P | RRRCPIVVIRVCRR | 9 |
| | Bac 3R, P, (V) | RRRLCPIVIRVCRR | 10 |
| | Bac 2R | RRLCRIVVIRVCRR | 11 |
| Hydrophobicity | Bac P | RLCRIVPVIRVCR | 12 |

TABLE I-continued

Amino Acid Sequences of Bactenecin and its Derivatives

| Peptide Classification | Name | Amino Acid Sequence | SEQ ID NO: |
|---|---|---|---|
| | Bac W | RLCRIVWVIRVCR | 13 |
| | Bac W, 2R | RRLCRIVWVIRVCRR | 14 |
| Others | Bac R, P, W | RRCPIVWVIRVCR-NH2 | 15 |
| | Bac 2R, 2P, W | RRCPIVWVIPVCRR-NH2 | 16 |
| | Bac-NH2 | RLCRIVVIRVCR-NH2 | 17 |
| | Bac 3I, 3V | RLCRIVVIRVCRIVIVIV | 18 |

EXAMPLE 2

MATERIAL AND METHODS

Bacterial Strains and Chemicals

Bacterial strains for antimicrobial activity testing included *Escherichia coli* UB1005 and its antibiotic super-susceptible derivative DC2 (Richmond et al., *Antimicrob. Agents Chemother.* 10:215, 1976), *Pseudomonas aeruginosa* K799 and its antibiotic-supersusceptible derivative Z61 (Angus et al., *Antimicrob. Agents Chemother.* 21:299, 1982), *Salmonella typhimurium* 14028s and its defensin-supersusceptible derivative MS7953s (Fields et al., *Science*, 243:1059, 1989), *Staphylococcus aureus* ATCC25923 and a clinical isolate *Staphylococcus aureus* SAP1007. Other Gram-positive bacterial strains include *Staphylococcus epidermidis* (clinical isolate) and *Enterococcus faecalis* ATCC29212, *Listeria monocytogenes*, *Corynebacterium xerosis*, *Streptococcus pneumoniae* ATTC49619, *Streptococcus pyogenes* ATTC19615, *Streptococcus mitis*.

Polymyxin B and 1-N-phenylnaphylamine (NPN) were purchased from Sigma (St. Louis, Mo.) 3,3-Dipropylthiacarbocyanine (DiS-C3-(5)) was from Molecular Probes (Eugene, Oreg.). Dansyl polymyxin B was synthesized as described previously (Schindler and Teuber, *Antimicrob. Agents Chemother.* 8:94, 1975). The lipids 1-pamitoyl-2-oleoyl-sn-glycero-3-phosphocholine (POPC) and 1-palmitoyl-2-oleoyl-sn-glycero-3-phospho-glycerol (POPG) were purchased from Northern Lipids Inc. (Vancouver, BC, Canada).

Synthesis and Refolding of Bactenecin

Bactenecin and its linear variant bac2S were synthesized by Fmoc (N-(9-fluorenyl) methoxycarbonyl) chemistry by the Nucleic Acid/Protein Service unit at the University of British Columbia using an Applied Biosystems, Inc. (Foster City, Calif.) Model 431 peptide synthesizer. The purchased bactenecin was in its fully reduced form. After a series of trials to determine the optimal strategy, the disulphide bond was formed by air-oxidation in 0.01M Tris buffer at room temperature for 24h. The concentration of bactenecin was kept below 100 µg/ml in the oxidation buffer to minimize the formation of multimers. A reversed phase column Pep RPC HR5/5 (Pharmacia; Quebec, Canada) was used to purify the disulphide-bonded bactenecin from the multimer by-product. The column was equilibrated with 0.3% (v/v) aqueous trifluoroacetic acid and eluted with a gradient of acetonitrile in 0.3% TFA at a flow rate of 0.7 ml/min. Peptide concentration was determined by amino acid analysis. Matrix-assisted laser desorption/ionization (MALDI)-mass spectrometry and acid-urea PAGE (Spiker, *Anal. Biochem.* 108:263, 1980) were used to confirm that the disulphide bond was properly formed, and a pure product obtained.

Circular Dichroism

A Jasco (Japan) J-720 spectropolarimeter was used to measure the circular dichroism spectra (Falla, *J. Biol. Chem.* 271:19298, 1996). The data was collected and analyzed by Jasco software. Liposomes POPC/POPG (7:3) were prepared by the freeze-thaw method to produce multilamellar vesicles as described previously (Mayer, *Biochim. Biophys. Acta*, 817:193, 1985), followed by extrusion through 0.1 mm double stacked Nuclepore filters using an extruder device (Lipex Biomembranes, Vancouver, BC Canada), resulting in unilamellar liposomes. Peptide at a final concentration of 50 mM was added to 100 mM liposomes, and incubated at room temperature for 10 min before the CD measurement.

Antimicrobial Activity

The minimal inhibitory concentration (MIC) of peptides was determined by a modified two-fold microtitre broth dilution method modified from that of Steinberg et al (Steinberg, *Antimicrob. Agents Chemother.* 41:1738, 1997). Using the classical method (Amsterdam, *Antibiotics in Laboratory Medicine* (Lorian, V., ed) pp. 72–78, 1991), higher concentrations of peptides tend to precipitate in the LB broth, thus the concentrations of peptides in the sequential wells are not accurate. Also the peptides stick to the most readily available (tissue-culture treated polystyrene) 96-well microtitre plates. Therefore the 2× series of dilutions was performed in Eppendoff tubes (polypropylene) before mixing with LB broth. Serial of two fold dilutions of peptides ranging from 640 µg/ml to 1.25 µg/ml were made in 0.2% BSA, 0.01% acetic acid buffer in the Eppendoff tubes. Ten µl of each concentration was added to each corresponding well of a 96-well microtiter plate (polypropylene cluster; Costar Corporation, Cambridge, Mass.). Bacteria were grown overnight and diluted 10–5 into fresh LB broth or Todd Hewitt broth for Streptococcus. LB medium contained 10 g/1l tryptone and 5 g/yeast extract, with no salt. Todd Hewitt contained 500 g/l beef heart infusion, 20 g/l bacto neopeptone, 2 g/l bacto dextrose, 2 g/l sodium chloride, 0.4 g/l disodium phosphate, 2.5 g/l sodium carbonate. One hundred ml of broth containing about 104–105 CFU/ml of tested bacteria was added to each well. The plate was incubated at 37° C. overnight. The MIC was taken as the concentration at which greater than 90% of growth inhibition was observed.

Dansyl-polymyxin B Displacement Assay

*E. coli* UB1005 LPS was prepared according to the phenol-chloroform-petroleum ether extraction method (Moore et al., *Antimicrob. Agents Chemother.* 29:496, 1986). The dansyl-polymyxin B displacement assay (American Society for Microbiology in *Methods for General Molecular Bacteriology*, pp. 91–92, 1994) was used to determine the relative binding affinity of peptides for LPS.

Membrane Permeabilization Assays

The ability of peptides to permeabilize the outer membrane was determined by the NPN assay of Loh et al. (Loh et al., *Antimicrob. Agents Chemother.* 19:777, 1984). Cytoplasmic membrane permeabilization was determined by using the membrane potential sensitive cyanine dye DiS-C3-(5) (Sims et al., *Biochemistry* 13:3315, 1974). The mutant *E. coli* DC2 with increased outer membrane permeability was used so that DiS-C3-(5) could reach the cytoplasmic membrane. Fresh LB medium was inoculated with an overnight culture, grown at 37° C., and mid-logarithmic phase cells (OD600=0.5–0.6) were collected. The cells were washed with buffer (5 mM HEPES, pH 7.2, 5 mM glucose) once, then resuspended in the same buffer to an OD600 of 0.05. The cell suspension was incubated with 0.2 mM DiS-C3-(5) until DiS-C3-(5) uptake was maximal (as indicated by a stable reduction in fluorescence due to fluorescence quenching as the dye became concentrated in the cell by the membrane potential), and 100 mM KCl was added to equilibrate the cytoplasmic and external K+ concentration. One ml cell culture was placed in a 1 cm cuvette and desired concentration of tested peptide was added. The fluorescence reading was monitored by using a Perkin-Elmer model 650-10 S fluorescence spectrophotometer (Perkin-Elmer Corp. Norwalk, Conn.), with an excitation wavelength of 622 nm and an emission wavelength of 670 nm. The maximal increase of fluorescence due to the disruption of the cytoplasmic membrane by certain concentration of cationic peptide was recorded. A blank with only cells and the dye was used to subtract the background. Control experiments titrating with valinomycin and K+ showed that the increase in fluorescence was directly proportional to the membrane potential and that a buffer concentration of 100 mM KCl prevented any effects of the high internal K+ concentration and corresponding opposing chemical gradient.

EXAMPLE 3

RESULTS

Bactenecin and its Linear Derivatives

The amino acid sequence of bactenecin and its linear derivatives are shown in Table I. The linear derivative (bac2S) with two cysteine residues replaced by two serine residues, was made to determine the importance of the disulphide bond in bactenecin's antimicrobial activity. The reduced form of bactenecin was also included in this study as a linear version of bactenecin. The identity of these peptides was confirmed by MALDI mass spectrometry. The MALDI data showed the molecular weight of the reduced bactenecin as 1486+1 dalton and oxidized bactenecin as 1484+1 dalton, in agreement with formation of one disulphide bond in the latter.

Circular Dichroism

Figure 1B:
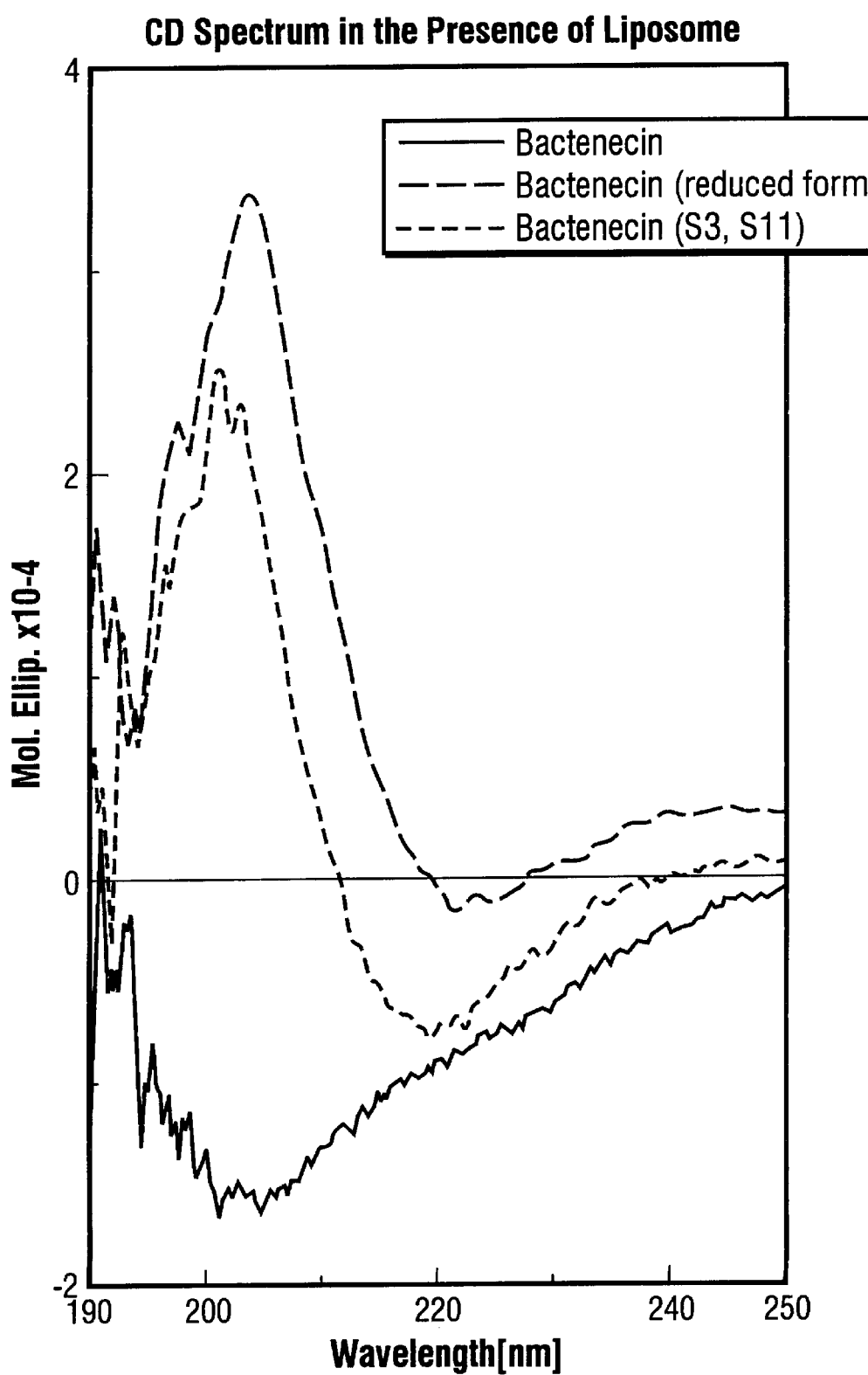
FIG. 1B shows the CD spectra of bactenecin in 10 mM sodium phosphate buffer (pH 7.0) in the presence of POPC/POPG.
Figure 1C:
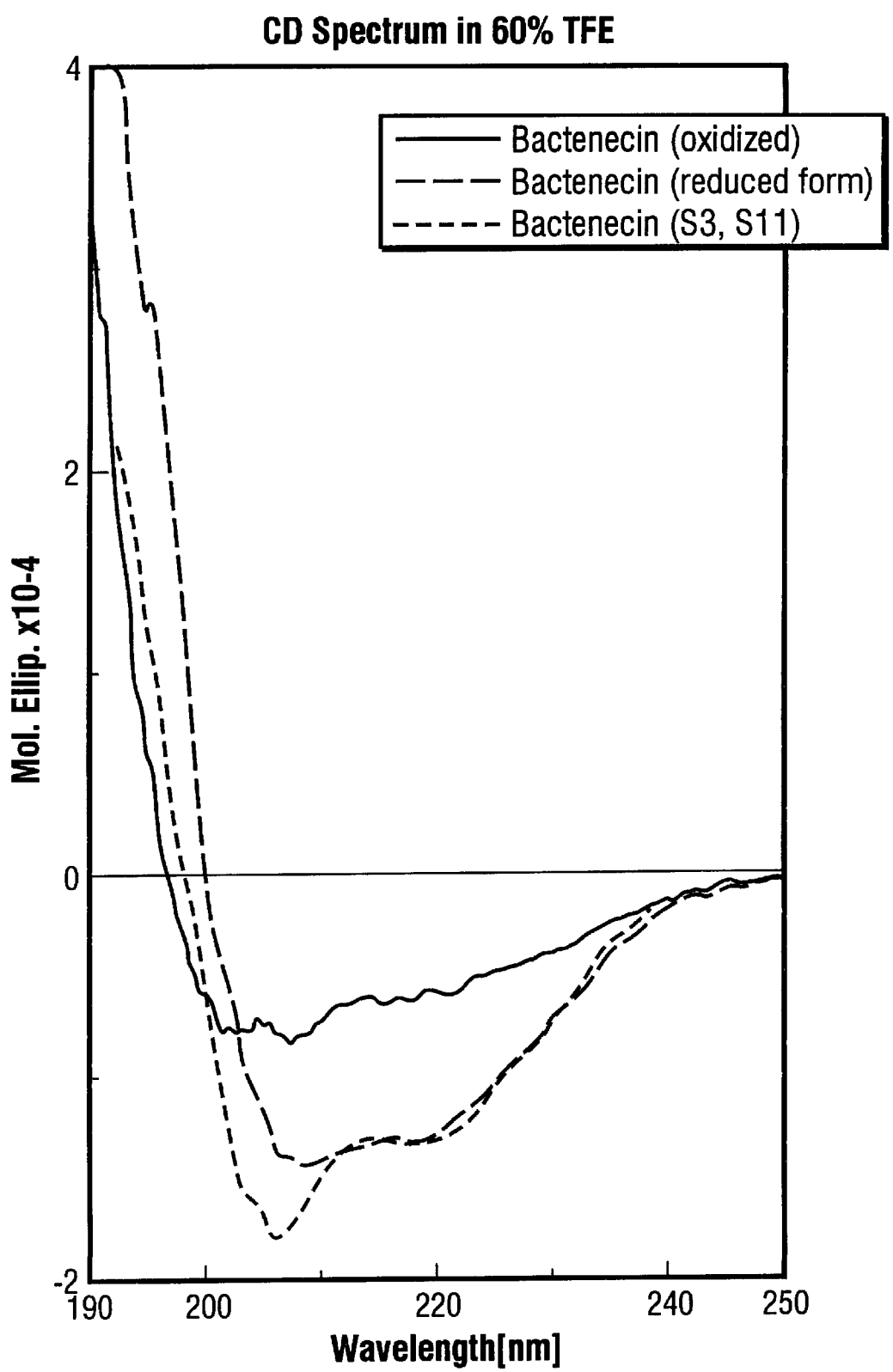
FIG. 1C shows the CD spectra of bactenecin in 10 mM sodium phosphate buffer (pH 7.0) in the presence of 60% (v/v) TFE.

Circular dichroism (CD) spectrometry (FIG. 1A) showed that bactenecin in the reduced form and bac2S was present in 10 mM sodium phosphate buffer as an unordered structure which had a strong negative ellipticity near 200 nm. Native bactenecin had a spectrum resembling oxyribonuclease and nuclease that are short polypeptides with a disulphide bond (Sims et al., *Biochemistry* 13:3315, 1974). The CD spectrum of bactenecin (FIG. 1A), demonstrated a negative ellipticity near 205 nm, typical of that seen for a type I β-turn structure (*Circular Dichroism and the conformational analysis of biomolecules* (Fasman G. D., ed) pp.318, 1996). In 60% TFE buffer, in the presence of liposomes and 10 mM SDS, the native bactenecin retained a similar structure (FIGS. 1B, 1C). However, the reduced form and bac2S exhibited clearly distinct structures from those observed in the aqueous solution. In 60% TFE buffer (considered an helix-inducing solvent), these two peptides tended to form α-helical structure (FIG. 1B), whereas and in the presence of liposomes (or 10 mM SDS), a β-sheet structure was evident (FIG. 1C). SDS micelles resemble the environment of lipid membranes.

Antimicrobial Activity

The MIC of bactenecin and its derivatives against a range of bacteria was determined by using a modified broth dilution method. Derivatives of bactenecin (Table I) were made to study the importance of the disulphide bond, three of them were also amidated at the C-terminal. The reduced forms of all peptides in the other groups were also included as linear derivatives in the minimum inhibitory concentration (MIC) test (Table IIC and IID). The MIC results showed that linearization changed the antimicrobial spectrum, linear derivatives were more active against Gram-positive bacteria than the native bactenecin (Table IIB, IID). The three amidated linear derivatives Bac 2A-NH2, Bac S-NH2, Bac 2S-NH2 also retained comparable activities against Gram-negative bacteria (Table IIA) with the native form. Bac 2A-NH2 was the most active one in this group. Its small size (12 amino acids long) also contributed to its interest as a prospective human antibiotic.

Eight derivatives had either additional positive charges or had the position of their positive charges rearranged. All had similar or better MIC values compared to the native bactenecin against Gram-negative and Gram-positive bacteria (Table IIIB). Three were constructed with 2 added positive charges: several of these derivatives with or without amidated C-terminuses had 4-fold better MICs against *E-coli* than native bactenecin (Table IIIA). Bac 2R was the best one in this group. Its MIC values against *P. aeruginosa* and *S. typhimurium* were also 2X better than the native bactenecin and it had better Gram positive specific activities.

Three derivatives with hydrophobicity changed were the last group, and the most interesting one. Bac W, Bac W, 2R showed excellent activities against Gram-positive bacteria (Table IVB) while Bac W kept the activities against Gram-negative bacteria, Bac W, 2R also showed good activities against Gram-negative bacteria (Table IVA). Table V showed the ability of bactenecin and its linear derivatives to lyse human red blood cells. Only Bac (reduced) and Bac W, 2R caused agglutination of human red blood cells at 16–32 mg/ml, which is higher than their MIC values. And it seemed that disulphide bond reduced the activity against red blood cells. Bac 2A, Bac S-NH2, Bac 2S-NH2, Bac W and Bac W, 2P showed growth inhibiting activities against some clinically significant bacteria, (e.g., *S. aureus, E. facaelis, S. pyogenes* and *S. pneumoniae*) whereas Bac 2R and Bac 2R,W were effective antimicrobials vs. clinically-significant Gram negative bacteria.

TABLE IIA

MIC Values (µg/ml) of Linear (Group1) Bactenecin Derivatives Against Gram-Negative Bacteria

| Peptide | *E.coli* UB1005 | *P.aeruginosa* | *S.typhimurium* | No. of Positive Charges |
|---|---|---|---|---|
| Bac 2A-NH2 | 4 | 8 | 32 | 5 |
| Bac S-NH2 | 4 | 16 | >64 | 5 |
| Bac 2S-NH2 | 2 | 16 | 32 | 5 |
| Bac 2S | 16 (32) | >64 | >64 | 4 |
| Bac (Reduced) | 64 | >64 | >64 | 4 |
| Bac (Oxidized) | 8 | 8 | 8 | 4 |

TABLE IIB

MIC Values (μg/ml) of Linear Bactenecin Derivatives (Group 1) Against Gram-Positive Bacteria

| Peptide | Staph. aureus | Staph. epidermidis | E.facaelis | Listeria | C. xerosis | Strep. pyogenes | Strep. mitis | Strep. pneumoniae |
|---|---|---|---|---|---|---|---|---|
| Bac 2A-NH2 | 4 | 1 | 2 | 0.25 | 0.25 | 2 | 0.25 | 16 |
| Bac S-NH2 | 16 | 2 | 16 | 0.5 | 0.5 | 8 | 0.5 | 8 |
| Bac 2S-NH2 | 4 | 1 | 4 | 0.25 | 0.25 | 2 | 0.125 | 16 |
| Bac 2S | 16 | 8 | 8 | 1 | 0.5 | 16 | 0.5 | >64 |
| Bac (Reduced) | >64 | 8 | 8 | 1 | 1 | 16 | 1 | 4 |
| Bac (Oxidized) | 32–64 | >64 | >64 | 8 | 1 | 16 | 2 | >64 |

*Listeria = Listeria monocytogenes, Staph. = Staphylococcus, E. = Enterococcus, C. = Corynybacterium, Strep = Streptococcus.*

TABLE IIC

MIC Values (μg/ml) of Linear (Group 2) Bactenecin Derivatives Against Gram-Negative Bacteria

| Peptide | E.coli UB1005 | P. aeruginosa | S. typhimurium | Length of amino acids | No. of positive Charges |
|---|---|---|---|---|---|
| Bac (Reduced) | 64 | >64 | >64 | 12 | 4 |
| Bac 3K, P | >64 | >64 | >64 | 12 | 4(3 K, 1R) |
| Bac 3R, P | 8 | >64 | >64 | 14 | 6 |
| Bac 3R, P, (V) | 4 | 32 | 32 | 13 | 6 |
| Bac P | 16 | 32 | 64 | 13 | 4 |
| Bac W | >64 | >64 | 64 | 13 | 4 |
| Bac 2R | 4 | 16 | 32 | 14 | 6 |
| Bac 2R, W | >64 | >64 | >64 | 15 | 6 |
| Bac (Oxidized) | 8 | 8 | 8 | 12 | 4 |

TABLE IIA

MIC Values (μg/ml) of Non-linear (Positive-Charge Modification Derivatives) Bactenecin Derivatives Against Gram-Negative Bacteria

| Peptide | E.coli UB1005 | P.aeruginosa | S.typhimurium |
|---|---|---|---|
| Bac 3K, P | 16 | >64 | 32 |
| Bac 3R, P | 2 | 8 | 8 |
| Bac 3R, P, (V) | 2 | 8 | 8 |
| Bac 2R | 2 | 4 | 4 |
| Bac R, P-NH2 | 2 | 16 | 16 |
| Bac R, P | 4 | ≥32 | 16 |
| Bac 21-NH2 | 4 | 16 | 8 |
| Bac 2R, P-NH2 | 4 | 16 | 32 |
| Bactenecin | 8 | 8 | 8 |

TABLE IID

MIC Values (μg/ml) of Linear (Group 2) Bactenecin Against Gram-Positive Bacteria

| Peptide | Staph. aureus | Staph. epidermidis | E.facaelis | Listeria | C. xerosis | Strep. pyogenes | Strep. mitis | Strep. pneumonia |
|---|---|---|---|---|---|---|---|---|
| Bac (Reduced) | >64 | 8 | 8 | 1 | 1 | 16 | 1 | 4 |
| Bac 3K, P | >64 | >64 | >64 | 4 | 4 | 64 | 0.25 | >64 |
| Bac 3R, P | >64 | 16 | 64 | 2 | 0.5 | 16 | 0.5 | >64 |
| Bac 3R, P, (V) | >64 | 8 | 32 | 1 | 0.5 | 8 | 1 | >64 |
| Bac P | >64 | 16 | 32 | 4 | 2 | 32 | 2 | >64 |
| Bac W | >64 | 32 | 32 | 2 | 1 | 16 | 1 | 32 |
| Bac 2R | >64 | 4 | 4 | 0.5 | 0.25 | 16 | 0.5 | >64 |
| Bac 2R, W | >64 | 32 | >64 | 4 | 2 | 32 | 2 | 64 |
| Bac (Oxidized) | 32–64 | >64 | >64 | 8 | 1 | 16 | 2 | >64 |

TABLE IIIB

MIC Values (μg/ml) of Non-linear (Positive-Charge Modification Derivatives) Bactenecin Derivatives Against Gram-Positive Bacteria

| | Staph. aureus | Staph. epidermidis | E.facaelis | Listeria | C. xerosis | Strep. pyogenes | S. mitis | S. pneumonia |
|---|---|---|---|---|---|---|---|---|
| Bac 3K, P | >64 | >64 | >64 | 8 | 16 | >64 | 2 | >64 |
| Bac 3R, P | >64 | 16 | 32 | 0.5 | 4 | 8 | 1 | >64 |
| Bac 3R, P, (V) | >64 | 16 | >64 | 1 | 4 | 4 | 1 | >64 |
| Bac 2R | 64 | 8 | 32 | <0.125 | 1 | 8 | 0.5 | >64 |
| Bac R, P-NH2 | 32–64 | 32 | >64 | 1 | 2 | 16 | 2 | >64 |
| Bac R, P | 32 | >32 | >32 | 8 | 16 | >64 | 16 | >64 |
| Bac 2I-NH2 | 32 | 8 | >32 | — | — | — | — | — |
| Bac 2R,P-NH2 | >32 | 16 | >32 | — | — | — | — | — |
| Bactenecin | 32–64 | >64 | >64 | 1 | 8 | 16 | 2 | >64 |

TABLE IVA

MIC Values (μg/ml) of Non-linear (Hydrophobicity Modification Derivatives) Bactenecin Derivatives Against Gram-Negative Bacteria.

| | MIC (μg/ml) | | |
|---|---|---|---|
| Peptide | E. coli UB1005 | P. aeruginosa | S. typhimurium |
| Bac P | 32 | >64 | >64 |
| Bac W | 8 | 4 | 4 |
| Bac 2R, W | 2 | 2 | 2 |
| Bactenecin | 8 | 8 | 8 |

TABLE IVB

MIC Values (μg/ml) of Non-Linear (Hydrophobicity Modification Derivatives) Bactenecin Derivatives Against Gram-Positive Bacteria

| Peptide | Staph. aureus | Staph. epidermidis | E.facaelis | Listeria | C. xerosis | Strep. pyogenes | S. mitis | S. pneumoniae |
|---|---|---|---|---|---|---|---|---|
| Bac P | 64 | 64 | >64 | 2 | 8 | 64 | 4 | >64 |
| Bac W | 4 | 2 | 8 | 0.5 | 1 | 2 | 1 | 16 |
| Bac 2R, W | 2 | 1 | 2 | 0.25 | 0.25 | 1 | 0.25 | 8 |
| Bactenecin | 32–64 | >64 | >64 | 1 | 8 | 16 | 2 | >64 |

TABLE V

Cell agglutinating activities of Bactenecin and its Derivatives on Human Red Blood Cells

| | Minimal Agglutinating Concentration (μg/ml) | |
|---|---|---|
| Peptide | Oxidized Form | Reduced Form |
| Bac 2A-NH2 | >64 | — |
| Bac S-NH2 | >64 | — |
| Bac 2S-NH2 | >64 | — |
| Bac 2S | >64 | — |
| Bactenecin (Reduced) | 16 | — |
| Bac R, P-NH2 | >64 | — |
| Bac R, P | >64 | — |
| Bac 3K, P | >64 | 64 |
| Bac 3R, P | 64 | 16 |
| Bac 3R, P, (V) | >64 | 32 |
| Bac P | 64 | 64 |
| Bac W | 32 | 4 |
| Bac 2R | 64 | 32 |
| Bac 2R, W | 32 | 8 |
| Bac 2I-NH2 | 32 | — |
| Bac 2R, P-NH2 | >32 | — |
| Bactenecin (Oxidized) | 64 | — |

Binding of Bactenecins to Purified E. coli UB1005

The MIC results indicated that the interaction with the outer membrane might be critical in the difference in antimicrobial activity against Gram negative bacteria among three bactenecin forms. The first step of cationic peptide antimicrobial action has been shown to involve the binding of the cationic peptide to the negatively charged surface of the target cells (Hancock et al., Adv. Microb. Physiol. 37:135, 1995). In Gram negative bacteria, this initial interaction occurs between the cationic peptides and the negatively charged LPS in the outer membrane (Falla et al., J. Biol. Chem. 271:19298, 1996; Sawyer et al., Infect. Immun.

Figure 2:
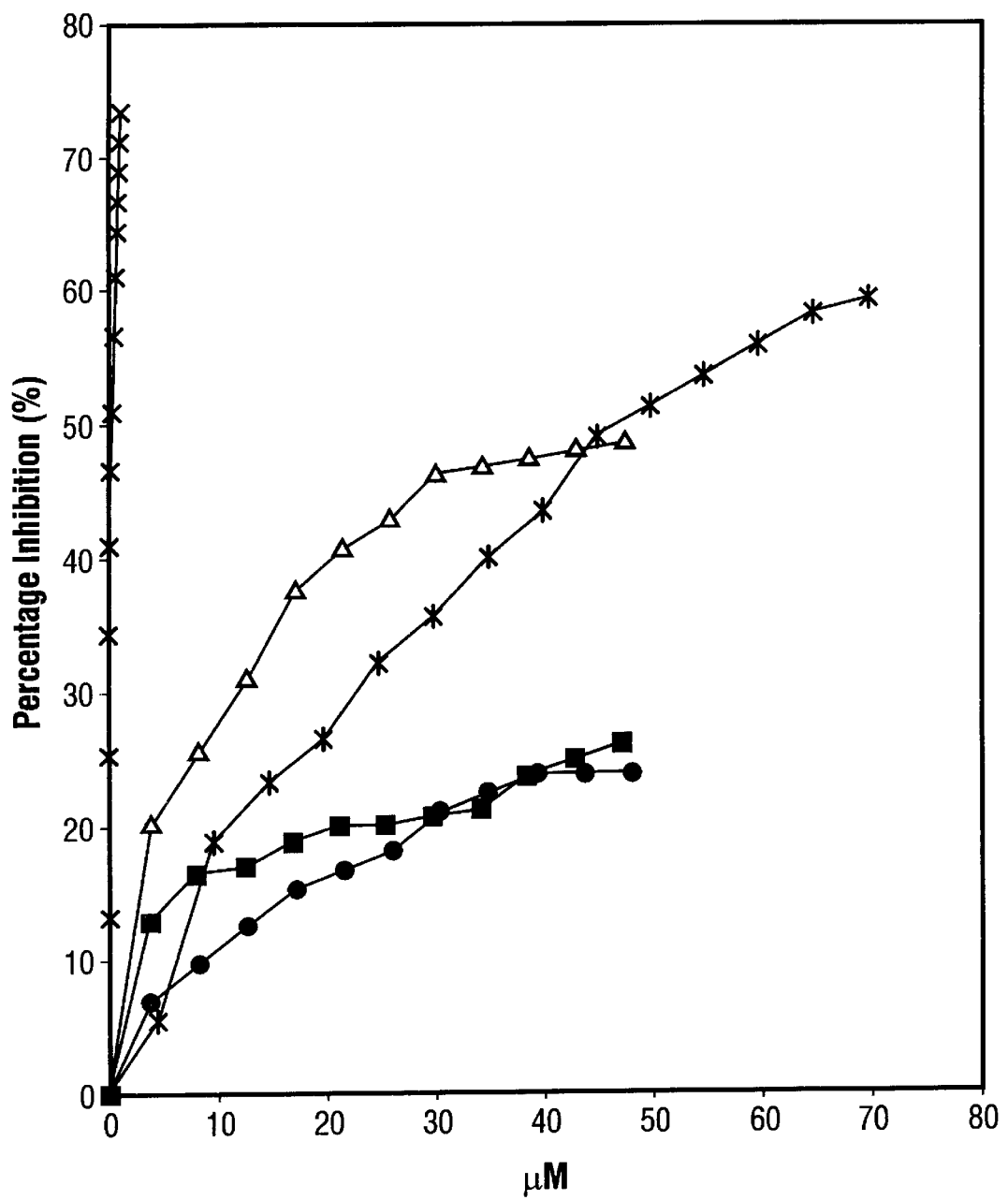
FIG. 2 shows a graph of the binding of peptides to LPS as assessed by their ability to displace dansyl polymyxin B from *E. coli* UB1005 LPS. Dansyl-polymyxin B was added to 1 ml of 3 μg/ml LPS to a final concentration of 1 μM which saturated the binding sites on LPS, and the fluorescence sensitivity was adjusted to 90%. The peptides and Mg2+ were titrated in resulting in a decrease in fluorescence due to dansyl polymyxin displacement until no decrease or very small decrease was detected. Polymyxin B: -x-; MgCl2: -*-; Bactenecin: -Δ-; Bac2S -■-; Bactenecin (reduced): -●-.

56:693, 1988; Piers and Hancock, *Mol. Microbio.* 12:951, 1994). Such binding can be quantified using the dansyl polymyxin B displacement assay. Dansyl polymyxin B is a fluorescently tagged cationic lipopeptide, which is non-fluorescent in free solution, but fluoresces strongly when it binds to LPS. When the peptides bind to LPS, they displace dansyl polymyxin B resulting in decreased fluorescence, which can be assessed as a function of peptide concentration (FIG. 2). Bactenecin was a relatively weak LPS-binder compared to polymyxin B, but it was still better than $Mg^{2+}$, the native divalent cation associated with LPS. Most importantly, it seemed that native bactenecin bound to LPS far better than its linear derivative and reduced form, which partially explained the difference in activities against Gram negative bacteria.

Effect on Outer Membrane Permeability

Figure 3:
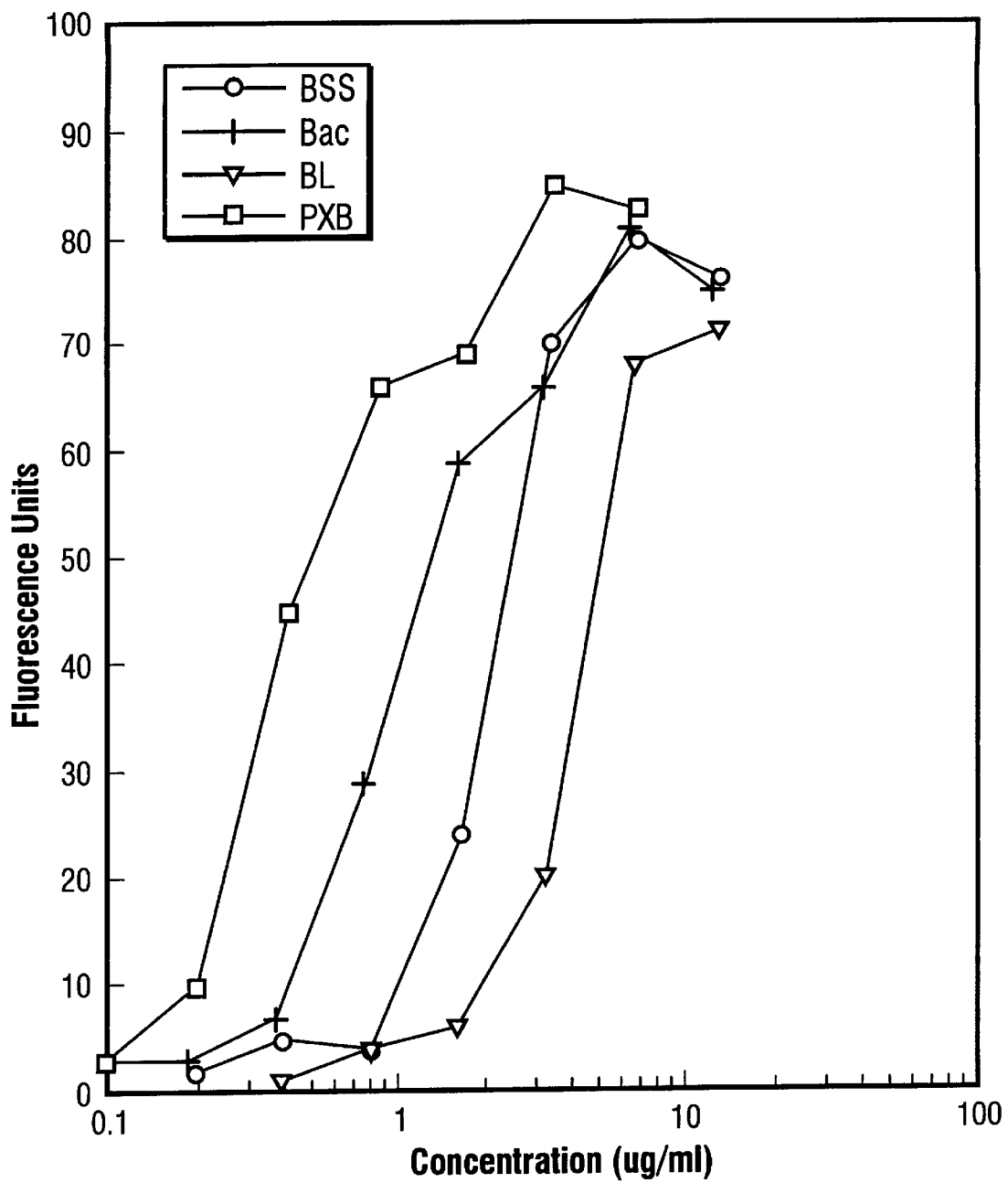
FIG. 3 shows peptide-induced outer membrane permeabilization measured by the NPN uptake in *E. coli* UB1005. Mid-log phase *E. coli* cells were collected and incubated with NPN in the presence of various concentrations of bactenecin (oxidized), bac2S, bactenecin (reduced). NPN was taken up into cells when the outer membrane was disrupted by the peptides. The uptake of NPN was measured by the increase of fluorescence. Polymyxin B: -□-; Bactenecin: -+-; Bac2S: -o-; Bactenecin (Reduced): -▽-
Figure 4:
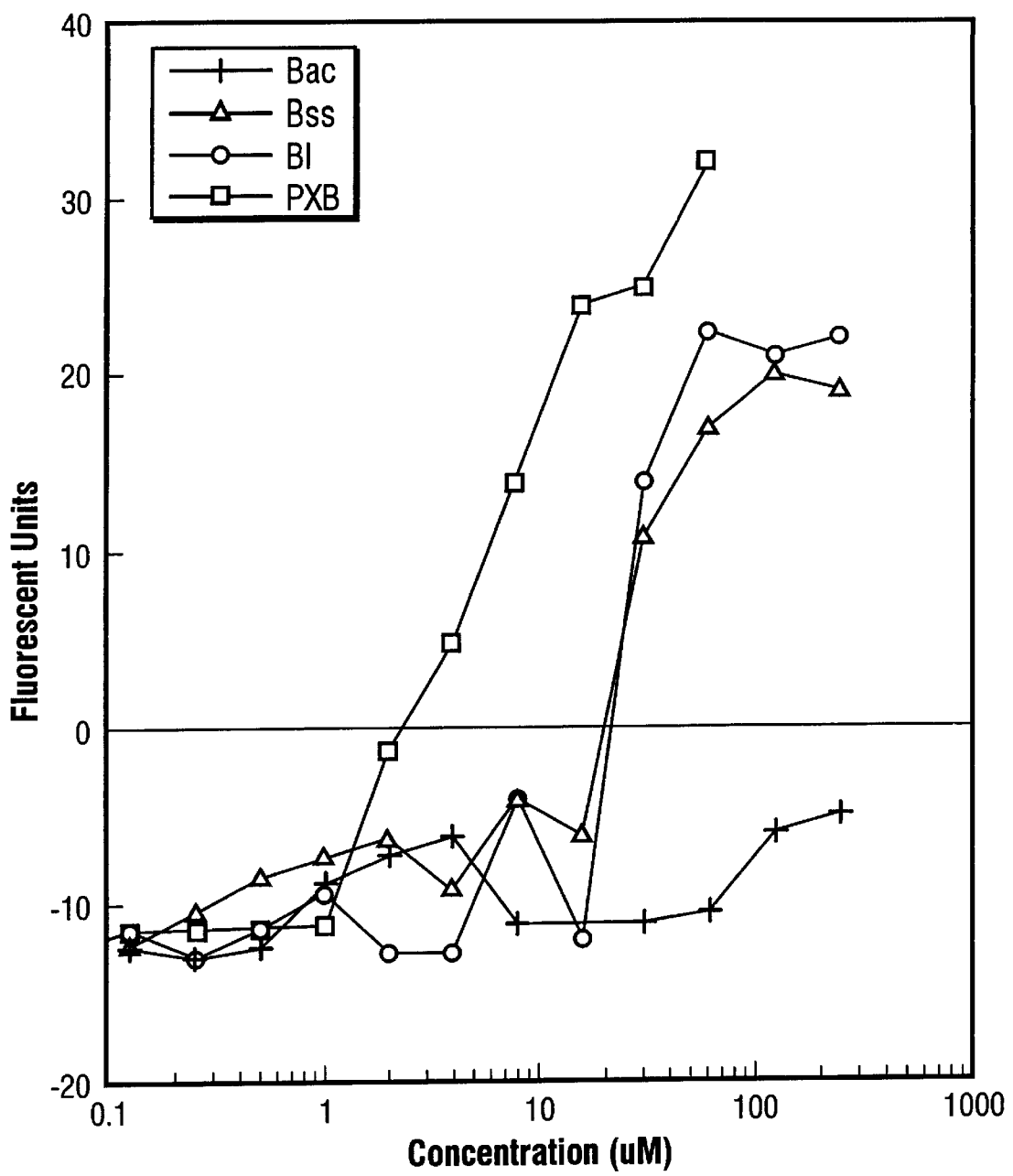
FIG. 4 shows the effect of peptide-induced inner membrane permeabilization measured by the DiS-C3-(5) assay. Mid-log phase cells were collected and resuspended in buffer (5 mM HEPE, 5 mM glucose) so that OD600=0.05. 0.2 mM final concentration of DiS-C3-(5 ) were incubated with cell suspension until no more quench was detected, then 0.1M KCL was added. Desired peptide concentration was added to 1 cm cuvette containing 1 ml cell suspension. The fluorescence change was observed until the equilibrium was reached. The fluorescence were taken as arbitrary units. MIC concentrations were indicated by arrows. Polymyxin: -□-; Bactenecin: -+-; Bac2S: -Δ-; Bactenecin(reduced): -○-.

Antimicrobial peptides bind to LPS, displacing the native divalent cations. Due to their bulky nature they disrupt the outer membrane and self-promote their own uptake across the outer membrane. In order to determine whether better binding ability resulted in better outer membrane permeabilization, a NPN assay was performed. NPN is a neutral hydrophobic probe that is excluded by an intact outer membrane, but is taken up into the membrane interior of an outer membrane that is disrupted by antimicrobial peptide action. NPN fluoresces weakly in free solution but strongly when it enters the membrane. FIG. 3 showed that polymyxin B permeabilized the outer membrane to 50% of maximal increase in fluorescence arbitrary units at 0.4 mg/ml, while bactenecin, bac2S and linear bactenecin caused half maximal permeabilization at 0.8 µg/ml, 2 µg/ml and 4.5 µg/ml respectively. Bactenecin was thus better than the linearized derivative and its reduced form at permeabilizing the outer membrane of *E. coli* UB1005.

Effect on Inner Membrane Potential Gradient

It has been proposed that the antibacterial target of cationic peptides be at the cytoplasmic membrane. Cationic peptides are generally able to interact electrostatically with the negatively charged headgroups of bacterial phospholipids and then insert into the cytoplasmic membrane, forming channels or pores which are proposed to lead to the leakage of cell contents and cell death. However there is very little data for peptides pertaining to measurement of the disruption of the cytoplasmic membrane permeability barrier, despite ample evidence that membrane disruption can occur in model membrane systems. Previous methods have utilized measurements of the accessibility of a normally-membrane-impermeable substrate to cytoplasmic β-galactosidase, this assay suffers from using a bulky substrate (ortho nitrophenyl galactoside). To circumvent this an assay was developed involving the membrane potential sensitive dye diS-C3-(5) to measure the disruption of electrical potential gradients in intact bacteria. The use of the *E. coli* mutant DC2 permitted us to perform this assay in the absence of EDTA. The fluorescent probe diS-C3-(5), which is a caged cation, distributes between cells and medium depending on the cytoplasmic membrane potential. Once inside the cells, diS-C3-(5) becomes concentrated and self-quenches its own fluorescence. If peptides form channels or otherwise disrupt the membrane, the membrane potential will be dissipated, and the DiS-C3-(5) will be released into the medium causing the fluorescence to increase, as can be detected by fluorescent spectrometry. In these assays, 0.1M KCl was added to the buffer to balance the chemical potential of K+ inside and outside the cells. Therefore the MICs of bactenecin, reduced bactenecin and bac2S in the presence of 0.1M KCl were determined and shown to be 8–16 µg/ml (i.e. 4 to 8 fold higher than in low salt). Despite these similar MICs for the 3 peptides vs. *E. coli* DC2, the influence of different concentrations of these peptides on the membrane potential was quite different. The native bactenecin started to cause the release of probe at ½MIC concentrations, whereas its linear derivative bac2S and reduced bactenecin showed probe release (dissipation of membrane potential) at concentration well below the MIC concentration.

EXAMPLE 4

The α-helical and U-structured classes are two groups of antimicrobial polycationic peptides that have been well studied. Although their precise antimicrobial mechanism is somewhat unclear, it has been proposed that the outer and the cytoplasmic membranes of Gram negative bacteria are their primary and final targets respectively. They have been proposed to kill bacteria by first electrostatically interacting with the surface of the bacterial cytoplasmic membrane (after self promoted uptake across the outer membrane for Gram negative bacteria). Then under the influence of a membrane potential, they are proposed to insert into the membrane and form channels to leak internal constituents. However much of this mechanism is based on data from model membrane studies.

Bactenecin belongs to a group of cationic peptides with only one disulphide bond. Bactenecin was active against the wild type Gram negative bacteria *E. coli*, *P. aeruginosa* and *S. typhimurium*, whereas the linear derivative and reduced form were relatively inactive. All three forms were equally active against outer membrane efflux defective mutants. This observation indicated that the disulphide bond was important for interaction with the outer membrane as confirmed here. Bactenecin had a better binding ability for LPS and also permeabilized the outer membrane better, explaining its better activity vs. wild type Gram negative bacteria. Computer modeling of bactenecin with InsightII software (Biosym Technologies Inc., San Diego, Calif.) indicated that bactenecin was a loop molecule with a hydrophobic ring and a positively charged face constructed from the C- and N-terminal portions of the molecule. Such a conformation, which was consistent with the CD spectral studies (FIGS. 1A–C), may make bactenecin a more amphipathic molecule than the unstructured linear and reduced form which exist in solution as random structures.

CD spectra indicated that bactenecin existed as a rigid β-turn loop molecule regardless of its environment. The molecule will thus be too small to span the membrane and form pores or channels unless a multimer is involved. Therefore it was of interest to know how this molecule interacted with the cytoplasmic membrane, which was believed to be the final target of many cationic peptides. If bactenecin interacts with the cytoplasmic membrane, it should at a minimum make it proton-leaky, and thus dissipate the membrane potential. DiS-C3-(5) is a membrane potential dependent dye, which is released from cells when the membrane potential is disrupted, leading to fluorescence dequenching. Despite their equivalent MIC value against *E. coli* DC2, the pattern of interaction of bactenecin and its linear variants with the cytoplasmic membrane was quite different. The linear variants dissipated the cytoplasmic membrane potential at concentrations as low as 0.125 µg/ml, whereas native bactenecin had effects on membrane potential only at concentration ½ MIC whereas the maximal effect was only seen at 4 fold the MIC. The different conformations that these bactenecin peptides adopted when interacting with hydrophobic membranes may be responsible for these differences. Linear variants with a more flexible structure were able to interact with the inner membrane in a way different from the native bactenecin with a rigid cyclic structure.

Although the invention has been described with reference to the presently preferred embodiment, it should be understood that various modifications can be made without departing from the spirit of the invention. Accordingly, the invention is limited only by the following claims.

What is claimed is:

1. An isolated antimicrobial peptide of the formula A-C-R-I-V-X-V-I-R-V-C-B; wherein X=any non-polar amino acid;
A=2 or 3 amino acids from R, L, K or I;
B=2 amino acids from R, L, K or I; and
C may or may not be covalently bonded to C, amidated variations and conservative variations thereof.

2. An isolated antimicrobial peptide of the following amino acid sequence RRLCRIVWVIRVCRR and analogs, derivatives, amidated variations and conservative variations thereof.

* * * * *